United States Patent [19]

Reissenweber et al.

[11] 4,310,677

[45] Jan. 12, 1982

[54] PREPARATION OF ALKYL ANTHRANILATES

[75] Inventors: Gernot Reissenweber, Ludwigshafen; Dietrich Mangold, Neckargemuend, both of Fed. Rep. of Germany

[73] Assignee: BASF Aktiengesellschaft, Fed. Rep. of Germany

[21] Appl. No.: 217,453

[22] Filed: Dec. 17, 1980

[30] Foreign Application Priority Data

Jan. 17, 1980 [DE] Fed. Rep. of Germany ....... 3001579

[51] Int. Cl.$^3$ .................... C07C 79/46; C07C 101/54
[52] U.S. Cl. ....................... 560/22; 560/19; 560/46; 560/47
[58] Field of Search .................... 560/19, 22, 46, 47

[56] References Cited

U.S. PATENT DOCUMENTS

| | | | |
|---|---|---|---|
| 2,170,185 | 8/1939 | Carpenter | 560/19 |
| 2,653,971 | 9/1953 | Balch | 562/458 |
| 3,621,017 | 11/1971 | Zeidler et al. | 71/91 |
| 3,625,989 | 12/1971 | Fields | 560/19 |
| 4,135,050 | 1/1979 | Hess et al. | 560/19 |

OTHER PUBLICATIONS

Wager et al., Synthetic Organic Chem., John Wiley & Sons, Inc., N.Y., pp. 480-481, 1965.
Rodd, Chem. of Carbon Compounds, vol. IIIa, p. 578 (Elsevier Publishing Co., N.Y. 1954).
Staiger et al., J. Org. Chem., vol. 24 (1959), pp. 1214-1219.
Coleman, J. Org. Chem., vol. 17, p. 173 (1952).

*Primary Examiner*—G. T. Breitenstein
*Attorney, Agent, or Firm*—Keil & Witherspoon

[57] ABSTRACT

Alkyl anthranilates are prepared by reacting an isatin with an alkanol and hydrogen peroxide in the presence of an alkali metal alkanolate.

The alkyl anthranilates obtainable by the process of the invention are valuable starting materials for the preparation of pesticides, dyes and drugs.

8 Claims, No Drawings

PREPARATION OF ALKYL ANTHRANILATES

The present invention relates to a novel process for the preparation of alkyl anthranilates by reacting an isatin with an alkanol and hydrogen peroxide in the presence of an alkali metal alkanolate.

It is known that esterification of anthranilic acids gives the corresponding anthranilic acid esters (Rodd, Chemistry of Carbon Compounds, Volume IIIa, page 578 (Elsevier, N.Y. 1954)). Equally, anthranilic acid esters are obtained by reacting an isatoic anhydride with an alcohol in the presence of sodium hydroxide (J. Org. Chem., 24 (1959), 1,214–1,219) or by reacting an isatoic anhydride with an alcoholic alcoholate solution. These esters are also obtained by reacting phthalimide with an alcoholic hypochlorite solution (Rodd, loc. cit.). A further method of preparing anthranilic acid esters is to nitrate a benzoic acid derivative, then reduce the nitro group, and thereafter carry out the esterification (Houben-Weyl, Methoden der Organischen Chemie, Volume 11/1, page 367).

These processes have disadvantages. Specifically substituted anthranilic acids or isatoic anhydrides are difficult to obtain and are as a rule prepared from correspondingly substituted isatins. Oxidation of isatins with hydrogen peroxide in dilute aqueous sodium hydroxide solution at 10°–15° C. gives anthranilic acids (Houben-Weyl, loc. cit., Volume 7/4, pages 30 and 31) and oxidation with chromium trioxide in acetic acid gives the corresponding isatoic anhydrides (J. Org. Chem., 17 (1952), 173), so that in total one extra reaction step is needed. Nitration of benzoic acid derivatives as a rule gives a product mixture which is difficult to separate. Thus, for example, the nitration of 3-methylbenzoic acid gives a mixture of 2-nitro, 4-nitro- and 6-nitro-3-methylbenzoic acid (Chem. Ber., 42 (1909), 430–431).

We have found that alkyl anthranilates of the formula

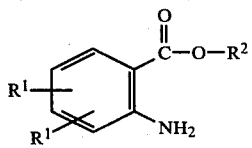

I where the $R^1$'s may be identical or different and each is hydrogen, halogen, an aliphatic radical, —$OR^3$ (where $R^3$ is an aliphatic radical) or nitro, and $R^2$ is an aliphatic radical are obtained advantageously when an isatin of the formula

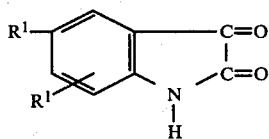

II where $R^1$ has the above meanings, is reacted with an alkanol of the formula $$R^2OH \qquad\qquad III$$

where $R^2$ has the above meaning, and hydrogen peroxide in the presence of an alkali metal alkanolate of the formula $$ZOR^2 \qquad\qquad IV$$

where Z is an alkali metal atom and $R^2$ has the above meaning.

Where isatin and methanol are used, the reaction can be represented by the following equation:

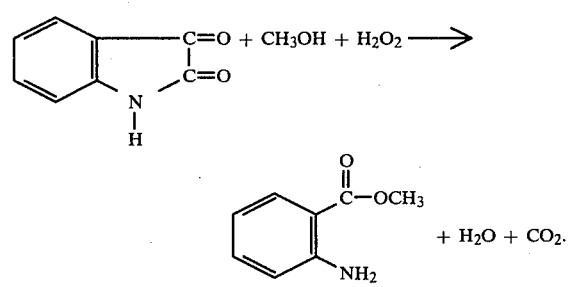

Compared to the conventional processes, the novel process gives alkyl anthranilates more simply and more economically, in good yield and high purity and, if the preparation of the starting material is taken into account, improved space/time yield. All these advantageous properties are surprisingly in view of the prior art.

The starting materials can be reacted with one another in the stoichiometric amounts or in an excess of any to the others; preferably, from 40 to 100, especially from 60 to 80, moles of alkanol III and/or from 1 to 3, especially from 1 to 1.5, moles of hydrogen peroxide are used per mole of isatin II. Preferred starting materials II and III and accordingly preferred end products I are those where the $R^1$'s are identical or different and each is hydrogen, bromine, chlorine, alkyl of 1 to 18, especially of 1 to 6, carbon atoms, haloalkyl of 1 to 18, especially 1 to 6, carbon atoms, and 1, 2 or 3 chlorine atoms, bromine atoms and/or fluorine atoms, or—$OR^3$, where $R^3$ is alkyl of 1 to 18, especially 1 to 6, carbon atoms, or $R^1$ is nitro, and $R^2$ is alkyl of 1 to 18, especially 1 to 6, carbon atoms. The above radicals may in addition be substituted by groups which are inert under the reaction conditions, for example alkyl or alkoxy, each of 1 to 4 carbon atoms.

Examples of isatins suitable for use as the starting material II are isatin itself, and isatin which is mono-substituted in the 4-, 5-, 6- or 7-position, or disubstituted in the 4,5-, 5,6-, 6,7-, 4,6-, 5,7-, or 4,7- positions (the substituents being identical or different), by bromine, chlorine, methyl, ethyl, propyl, isopropyl, butyl, isobutyl, sec.-butyl, tert.-butyl, methoxy, ethoxy, propoxy, isopropoxy, butoxy, isobutoxy, sec.-butoxy, tert.-butoxy, trifluoromethyl or nitro.

Examples of alkanols suitable for use as the starting material III are methyl, ethyl, propyl, butyl, isopropyl, sec.-butyl, tert.-butyl and isobutyl alcohol, of which methyl alcohol and ethyl alcohol are preferred.

The hydrogen peroxide is advantageously used in the form of an aqueous solution of 5–60, preferably 20–55, percent strength by weight. In some cases, materials which form hydrogen peroxide under the reaction conditions may also be used, for example inorganic or organic peroxy compounds, eg. sodium peroxide, potassium peroxide, magnesium peroxide, calcium peroxide, zinc peroxide and barium peroxide; hydroperoxides, eg.

NaOOH . 0.5 H₂O₂ and NH₄OOH; corresponding hydrates, eg. CaO₂ . 8H₂O, and peroxy hydrates, eg. BaO₂ . H₂O₂ . 2H₂O₂; sodium peroxydisulfate, potassium peroxydisulfate and ammonium peroxydisulfate. It is also possible to use hydrogen peroxide adduct, such as sodium borate peroxyhydrate. Where appropriate, auxiliaries such as magnesium sulfate or magnesium chloride may also be used.

Preferred alkali metal alkanolates IV are those where $R^2$ has the above preferred meaning; examples include the alkali metal alkanolates of the alkanols III mentioned as examples of suitable alkanols. As a rule, a particular alkanol III and its corresponding alkali metal alkanolate IV are used together. Preferred alkanolates are the potassium alkanolate and sodium alkanolate. The alkanolates IV can be used in the stoichiometric amount or in excess, preferably in an amount of from 1 to 5, especially 2 to 3, moles of alkanolate IV per mole of starting material II. Instead of the alkanolates IV, compounds which form alkanolates under the reaction conditions, eg. the alkanol and an alkali metal hydride, may be used.

The reaction is advantageously carried out at from $-50°$ to $+80°$ C., preferably from $-10$ to $+50°$ C., under atmospheric or superatmospheric pressure, continuously or batchwise. In the case of a liquid alkanol III, especially an alkanol of 1 to 4 carbon atoms, the reaction mixture is advantageously used as the solution medium, and an additional solvent is not employed. Where appropriate, however, a solvent which is inert under the reaction conditions is used. Examples of suitable solvents are aromatic hydrocarbons, eg. toluene, ethylbenzene, o-, m- and p-xylene, isopropylbenzene and methylnaphthalene; halohydrocarbons, eg. chlorobenzene, fluorobenzene, bromobenzene, iodobenzene, o-, p- and m-dichlorobenzene, o-, p- and m-dibromobenzene, o-, m- and p-chlorotoluene; 1,2,4-trichlorobenzene, 1,10-dibromodecane and 1,4-dibromobutane; nitrohydrocarbons, eg. nitromethane, nitroethane, nitrobenzene, o-, m- and p-chloronitrobenzene and o-nitrotoluene; sulfoxides, eg. dimethylsulfoxide and diethylsulfoxide, and sulfones, eg. dimethylsulfone, diethylsulfone, methylethylsulfone and tetramethylenesulfone; dimethylformamide; and mixtures of the above. Advantageously, the solvent is used in an amount of from 400 to 10,000 percent by weight, preferably from 600 to 1,000 percent by weight, based on starting material II.

The reaction may be carried out as follows: the hydrogen peroxide, starting materials II and III, and compound IV, with or without a solvent, are kept at the reaction temperature for from 0.5 to 2 hours. The end product is then isolated from the mixture in a conventional manner, for example by fractional distillation. The end product may also be isolated by distilling off the solvent, taking up the residue in water, rendering the aqueous solution neutral, extracting it with methylene chloride and distilling the extract.

The alkyl anthranilates of the formula I obtainable by the novel process are valuable starting materials for the preparation of pesticides, dyes and drugs. For example, reaction of anthranilates with aminosulfonyl chlorides, followed by cyclization, gives benzothiadiazones (German Laid-Open Application DOS No. 2,443,901), which are known herbicides. Further, for example, reaction of anthranilates I with sulfamyl chlorides gives the o-sulfamidobenzoic acids described in German Laid-Open Application DOS No. 2,104,682. Cyclization of these compounds, for example by the process described in German Laid-Open Application DOS No. 2,105,687, gives 2,1,3-benzothiadiazin-4-one-2,2-dioxides, whose use as crop protection agents and drugs is described in the same DOS. The very good herbicidal properties of this category of compound are described in U.S. Pat. No. 3,621,017, German Pat. No. 1,937,551 and German Laid-Open Application DOS No. 2,131,401.

The end products I may also be used as additives in perfumes, sun oils, burn ointments and as aging stabilizers in synthetic rubber. Concerning further uses, reference may be made to the above publications and to Ullmanns Encyklopädie der technischen Chemie, Volume 8, page 375.

In the Examples which follow, parts are by weight and bear the same relation to parts by volume as that of the kilogram to the liter.

EXAMPLE 1

20 parts of a 30 percent strength by weight solution of sodium methylate in methanol are added to a suspension of 14.7 parts of isatin in 200 parts of methanol at 0° C. 8 parts of 50 percent strength by weight aqueous hydrogen peroxide solution are then added, whilst cooling at $-3°$ C., in the course of which the initially dark violet solution loses its color. The mixture is stirred for 30 minutes at room temperature, the solvent is evaporated off, water is added to the residue and the batch is extracted by shaking with methylene chloride. On evaporation of the methylene chloride, 12.4 parts (82% of theory) of methyl anthranilate, of melting point 21°–23° C., are obtained.

EXAMPLE 2

15 parts of 50 percent strength by weight hydrogen peroxide solution are added slowly to a solution of 32.2 parts of 7-methylisatin and 12 parts of sodium methylate in 400 parts of methanol at 0° C. Thereafter, the mixture is stirred for 2 hours at room temperature and worked up as described in Example 1. 25.5 parts (78% of theory) of methyl 3-methylanthranilate, of melting point 27°–29° C., are obtained.

EXAMPLE 3

20 parts of a 30 percent strength by weight solution of sodium methylate in methanol are added to 21.6 parts of 5,7-dichloroisatin in 300 parts of methanol at $-10°$ C., resulting in a dark violet suspension of a bulky precipitate. 7 parts of 50 percent strength by weight hydrogen peroxide solution are then added at $-3°$ C. and thereafter the mixture is stirred for one hour at room temperature. The solution is concentrated and the crystalline residue is mixed with water and filtered off. 17.6 parts (80% of theory) of methyl 3,5-dichloroanthranilate, of melting point 62°–63° C., are obtained.

EXAMPLE 4

Using a method similar to Example 3, 22.6 parts of 5-bromoisatin give 17.4 parts (76% of theory) of methyl 5-bromoanthranilate, of melting point 73°–74° C.

EXAMPLE 5

20 parts of a 30 percent strength by weight solution of sodium methylate in methanol and 8 parts of 50 percent strength by weight hydrogen peroxide solution are added successively to 19.2 parts of 5-nitroisatin in 300 parts of methanol at 0° C. After working up as described in Example 3, 16 parts (82% of theory) of methyl 5-nitroanthranilate, of melting point b 166°–168° C., are obtained.

EXAMPLE 6

20 parts of a 30 percent strength by weight solution of sodium methylate in methanol are added to 21.5 parts of 7-trifluoromethylisatin in 300 parts of methanol at 0° C., resulting in a violet solution. 8 parts of a 50 percent strength by weight hydrogen peroxide solution are then added at 0° C., after which the mixture is stirred for one hour at room temperature. The reddish solution is concentrated, water is added, the pH is brought to 8 with hydrochloric acid and the batch is extracted by shaking with methylene chloride. After concentrating the methylene chloride phase, 16.2 parts (74% of theory) of methyl 3-trifluoromethylanthranilate are obtained.

$H^1$—NMR (CDCl$_3$): $\delta$=3.8 ppm (s), 6.4 (s, N—H$_2$), 6.6 (t), 7.5 (d) and 7.95 (d).

EXAMPLE 7

8.6 parts of 50 percent strength by weight sodium hydride are added to 14.7 parts of isatin in 250 parts of n-butanol and 100 parts of dimethylformamide at 25° C. After one hour, 8 parts of 50 percent strength by weight hydrogen peroxide solution are slowly added to the violet solution, and the temperature is allowed to rise to 50° C. The mixture is then stirred for one hour and is worked up as described in Example 1. 10.8 parts (56% of theory) of n-butyl anthranilate are obtained.

$H^1$—NMR (CDCl$_3$): $\delta$=0.8–1.8 ppm (m, 7H); 4.1 (t, 2H); 6.2–7.6 (m, 5H); and 6.4 (s, NH$_2$).

We claim:

1. A process for the preparation of alkyl anthranilates of the formula

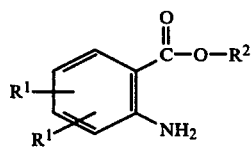

I where the $R^1$'s may be identical or different and each is hydrogen, halogen, an aliphatic radical, —$OR^3$ (where $R^3$ is an aliphatic radical) or nitro, and $R^2$ is an aliphatic radical, wherein an isatin of the formula

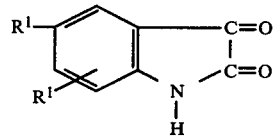

II where $R^1$ has the above meanings, is reacted with an alkanol of the formula $R^2OH$    III where $R^2$ has the above meaning, and hydrogen peroxide in the presence of an alkali metal alkanolate of the formula $ZOR^2$    IV where Z is an alkali metal atom and $R^2$ has the above meaning.

2. a process as claimed in claim 1, wherein the reaction is carried out with from 40 to 100 moles of alkanol III per mole of isatin II.

3. A process as claimed in claim 1, wherein the reaction is carried out with from 1 to 3 moles of hydrogen peroxide per mole of isatin II.

4. A process as claimed in claim 1, wherein the reaction is carried out with a 5–60 percent strength by weight aqueous solution of hydrogen peroxide.

5. A process as claimed in claim 1, wherein the reaction is carried out with from 1 to 5 moles of alkanolate IV per mole of starting material II.

6. A process as claimed in claim 1, wherein the reaction is carried out at from −50° to +80° C.

7. A process as claimed in claim 1, wherein the reaction is carried out at from −10° to +50° C.

8. A process as claimed in claim 1, wherein the reaction is carried out using a solvent which is inert under the reaction conditions.

* * * * *